United States Patent
Lassalle et al.

Patent Number: 5,453,430
Date of Patent: Sep. 26, 1995

[54] 1-[2-(ARYLSULPHONYLAMINO)-1-OXO-ETHYL]PIPERIDINE DERIVATIVES, THEIR PREPARATION AND THEIR THERAPEUTIC APPLICATION

[75] Inventors: Gilbert Lassalle, Clamart; Thomas Purcell, Montfort l'Amaury; Daniel Galtier, Saint Cyr l'Ecole; Paul H. Williams, Paris; Frédéric Galli, La Celle Saint Cloud, all of France

[73] Assignee: Synthelabo, Le Plessis Robinson, France

[21] Appl. No.: 37,972

[22] Filed: Mar. 29, 1993

[30] Foreign Application Priority Data

Mar. 30, 1992 [FR] France .................... 92 03828

[51] Int. Cl.⁶ .............. C07D 401/14; C07D 403/14; A61K 31/47
[52] U.S. Cl. .............................. 514/312; 546/153
[58] Field of Search ............... 546/153; 514/312

[56] References Cited

FOREIGN PATENT DOCUMENTS 0008746 3/1980 European Pat. Off. ........... 546/227

*Primary Examiner*—Alan L. Rotman
*Attorney, Agent, or Firm*—Jacobson, Price, Holman & Stern

[57] ABSTRACT

Compounds of formula (I)

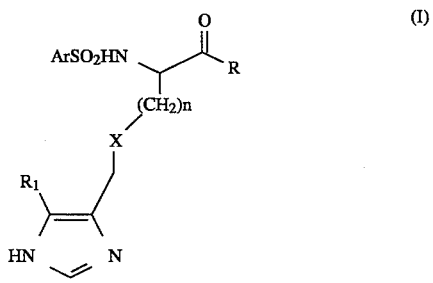

wherein R represents a

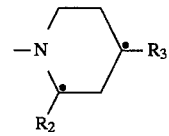

group in which $R_2$ is a hydrogen atom, a $(C_1-C_4)$alkoxycarbonyl group, a carboxylic group, a sodium carboxylate group, a —$CH_2OR_4$ group $R_4$ being a hydrogen atom or a $(C_1-C_4)$alkyl group or a $(C_1-C_4)$acyl group, an amide group of the formula —$CONR_5R_6$, or a —$CN_4R_5$ group, $R_5$ being a hydrogen atom or a $(C_1-C_4)$alkyl group and $R_6$ being a hydrogen atom, a $(C_1-C_4)$alkyl group, a hydroxy group or a $(C_1-C_4)$alkoxy group, and $R_3$ is a $(C_1-C_4)$alkyl group, $R_1$ represents either a hydrogen atom or a $(C_1-C_4)$alkyl group, X represents either a sulphur atom, an oxygen atom or a methylene group, n=1 or 2 and Ar represents either a naphthalen-1-yl group substituted by a di$(C_1-C_4)$alkylamino group, or a 6,7-di$(C_1-C_4)$alkoxynaphthalen-1-yl group, or a quinolin-8-yl group substituted at 3 by a $(C_1-C_4)$alkyl group, or a 1,2,3,4-tetrahydroquinolin-8-yl group substituted at 3 by a $(C_1-C_4)$alkyl, or a 1H-indazol-7-yl group and pharmaceutically acceptable organic or inorganic salts thereof.

Application in therapy.

5 Claims, No Drawings

1-[2-(ARYLSULPHONYLAMINO)-1-OXOETHYL]-PIPERIDINE DERIVATIVES, THEIR PREPARATION AND THEIR THERAPEUTIC APPLICATION

The present invention relates to 1-[2-(arylsulphonyl-lamino)-1-oxoethyl]piperdine derivatives, their preparation and their therapeutic application.

The compounds of the invention are of formula (I)

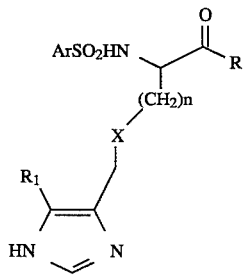

wherein R represents a

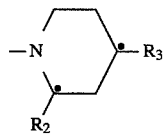

group in which $R_2$ is a hydrogen atom, a $(C_1-C_4)$alkoxycarbonyl group, a carboxylic group, a sodium carboxylate group, a —$CH_2OR_4$ group $R_4$ being a hydrogen atom or a $(C_1-C_4)$alkyl group or a $(C_1-C_4)$acyl group, an amide group of the formula —$CONR_5R_6$, or a —$CN_4R_5$ group, $R_5$ being a hydrogen atom or a $(C_1-C_4)$alkyl group and $R_6$ being a hydrogen atom, a $(C_1-C_4)$alkyl group, a hydroxy group or a $(C_1-C_4)$ alkoxy group, and $R_3$ is a $(C_1-C_4)$ alkyl group, $R_1$ represents either a hydrogen atom or a $(C_1-C_4)$alkyl group, X represents either a sulphur atom, an oxygen atom or a methylene group, n=1 or 2 and Ar represents either a naphthalen-1-yl group substituted by a di$(C_1-C_4)$alkylamino group, or a 6,7-di$(C_1-C_4)$alkoxynaphthalen-1-yl group, or a quinolin-8-yl group substituted at 3 by a $(C_1-C_4)$alkyl group, or a 1,2,3,4-tetrahydroquinolin-8-yl group substituted at 3 by a $(C_1-C_4)$alkyl, or a 1H-indazol-7-yl group.

The preferred compounds of the invention are those of formula (I) wherein R represents a

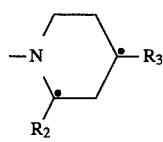

group in which $R_2$ is a hydrogen atom, a $(C_1-C_4)$alkoxycarbonyl group, a carboxylic group, a sodium carboxylate group, a —$CH_2OR_4$ group $R_4$ being a hydrogen atom or a $(C_1-C_4)$alkyl group or a $(C_1-C_4)$acyl group, an amide group of the formula —$CONR_5R_6$, or a —$CN_4R_5$ group, $R_5$ being a hydrogen atom or a $(C_1-C_4)$alkyl group and $R_6$ being a hydrogen atom, a $(C_1-C_4)$alkyl group, a hydroxy group or a $(C_1-C_4)$ alkoxy group, and $R_3$ is a $(C_1-C_4)$ alkyl group, $R_1$ represents either a hydrogen atom or a $(C_1-C_4)$alkyl group, X represents either a sulphur atom, an oxygen atom or a methylene group, n=1 or 2 and Ar represents either the 5-(dimethylamino)naphtalen-1-yl group, or the 6,7-dimethoxynaphthalen-1-yl group, or the 3-methylquinolin-8-yl group, or the 3-methyl-1,2,3,4-tetrahydroquinolin-8-yl group.

Of these compounds the preferred compounds of the invention are those of formula (I) wherein R represents a

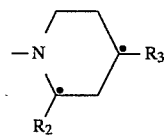

group in which $R_2$ is a carboxylic group, an ethoxycarbonyl group, a hydroxycarboxamide group, a hydroxymethyl group, or a 1H-tetrazolyl group, and $R_3$ is a methyl group or an ethyl group, $R_1$ is a hydrogen atom or a methyl group, X is a methylene group, n=1 and Ar is the 3-methyl-1,2,3,4-tetrahydroquinolin-8-yl radical.

The compounds of the invention have 3 asymmetric centers according to the meaning of the substituents.

The preferred configuration of the piperidinyl group is [2R,4R].

The preferred configuration of the asymmetric carbon in the central amino acid part

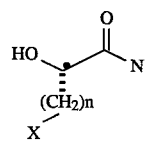

is [S].

There is also a fourth asymmetric center when Ar represents a 1,2,3,4-tetrahydroquinolin-8-yl group substituted at 3 by a $(C_1-C_4)$alkyl group. In this case the compounds are in the form of a mixture of diastereoisomers.

The compounds of the invention may be in the form of free bases or addition salts of pharmaceutically acceptable acids.

In the following synthetic schemes shown in diagrams 1 to 4, $R_1$, $R_2$, $R_3$ and Ar are as defined above, and Ts represents a 4-(methylphenyl)sulphonyl group.

The compounds of the invention in which X represents a methylene group are of formula (Ia)

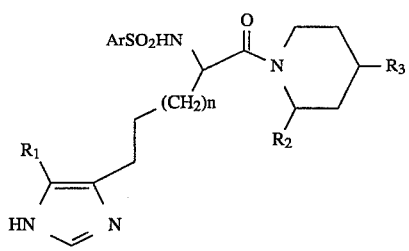

(Ia)

wherein n=1 or 2 and $R_1$, $R_2$, $R_3$ and Ar are as defined above; they may be synthesised as shown in diagram I on the following page.

In the first step, an alcohol of formula (II) is reacted with thionyl chloride in a mixture of dimethylformamide and dichloromethane, then the compound obtained is reacted with triphenylphosphine in a solvent such as dimethylformamide or benzene at a temperature of 80° C.; a phosphonium salt of formula (III) is obtained.

In the second step compound (III) is reacted with a compound of formula (IV); the reaction is carried out in a solvent such as tetrahydrofuran, in the presence of n-butyllithium at a temperature of −70° C. A compound of formula (V) is obtained as a mixture of cis and trans isomers around the double bond.

In the third step, compound (V) obtained is subjected to catalytic hydrogenation to obtain a compound of formula (VI). In the fourth step, this compound is reacted with an arylsulphonyl chloride of the formula $ArSO_2Cl$ in which Ar is as defined above, and a compound of formula (VII) is obtained; the reaction is carried out in a solvent such as chloroform or dichloromethane in the presence of a base such as triethylamine.

In the fifth step deprotection of the carboxylic moiety of compound (VII) is effected using hydrogen chloride, in a solvent such as benzene, to obtain a compound of formula (VIII).

In the sixth step compound (VIII) is condensed with a compound of formula (IX), and a compound of formula (X) is obtained. The reaction is carried out in the presence of a base such as N-methylmorpholine or N,N-diisopropylethylamine ("Hünig's base") and a coupling agent such as [(benzotriazol-1-yl)-oxy]tris(dimethylaminopropyl)-3-ethylcarbodiimide hydrochloride coupled with 1-hydroxybenzotriazole.

In the seventh step deprotection of the imidazole nucleus of compound (X) is effected, either by hydrogenation or by the action of acetic acid in a mixture of tetrahydrofuran and water. A compound of formula (Ia) is obtained. When a compound of formula (X), in which Ar represents the 3-methyl-quinolin-8-yl Diagram 1

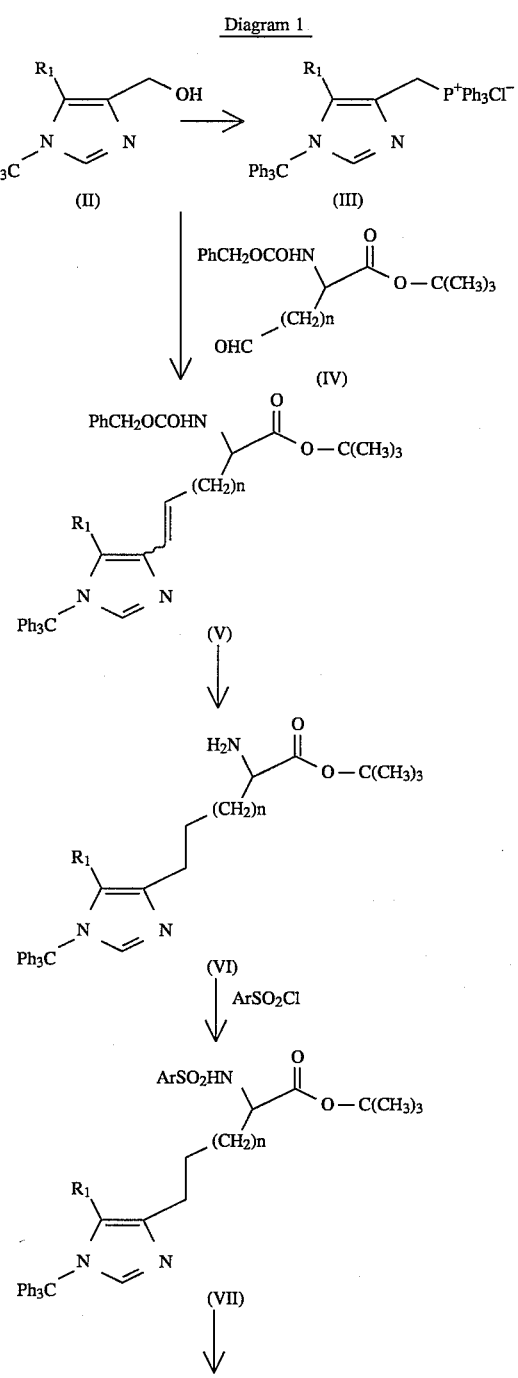

-continued
Diagram 1

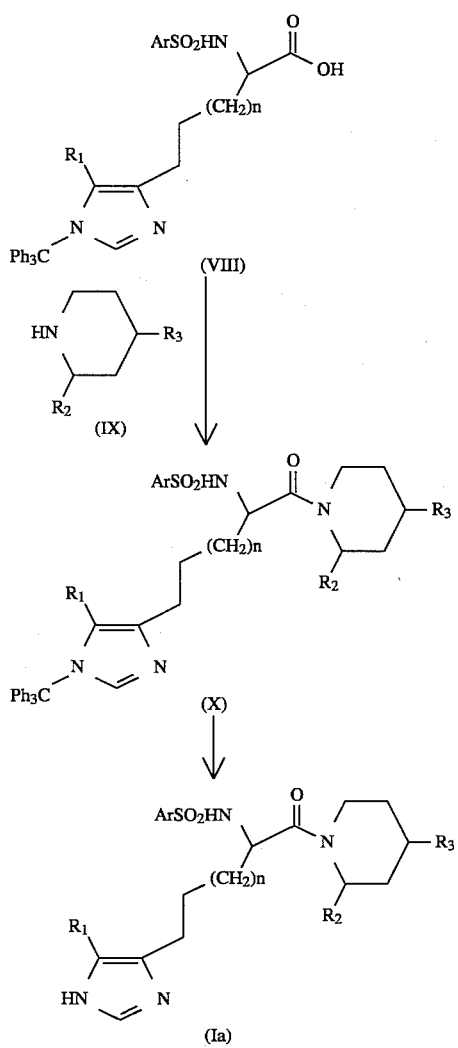

group, is hydrogenated with heating, compounds of formula (Ia) are obtained in which Ar is the 3-methyl-1,2,3,4-tetrahydroquinolin-8-yl group. When $R_2$ is a $(C_1-C_4)$ alkoxycarbonyl group, compound (Ia) may be reacted with a 1N aqueous solution of sodium hydroxide to obtain the sodium salt of the corresponding acid.

The compounds of the invention, in which X represents a sulphur atom, are of formula (Ib)

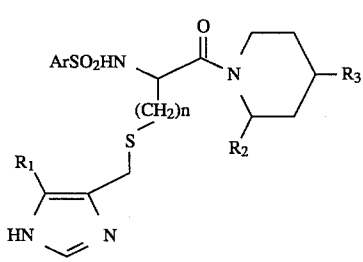

in which n=1 or 2 and $R_1$, $R_2$, $R_3$ and Ar are as defined above. The compounds of formula (Ib) in which n=1 may be synthesised as shown in diagram 2 on the following page.

In the first step, an alcohol of formula (II) is reacted with thionyl chloride in a mixture of dimethylformamide and dichloromethane, then the compound obtained is reacted with L-cysteine (XI), and a compound of formula (XII) is obtained; the reaction is carried out in a 1N aqueous solution of sodium hydroxide.

In the second step, the compound of formula (XII) is reacted with an arylsulphonyl chloride of the formula $ArSO_2Cl$, in which Ar is as defined above, and a compound of formula (XIII) is obtained; the reaction is carried out in basic conditions such as aqueous sodium hydroxide.

In the third step, compound (XIII) is condensed with a compound of formula (IX), and a compound of formula (XIV) is obtained. The reaction is carried out in the presence of a base such as N-methylmorpholine or N,N-diisopropylethylamine ("Hünig's base") and a coupling agent such as [(benzotriazol-1-yl)oxy]tris(dimethylamino)phosphonium hexafluorophosphate, diphenylphosphorylazide or 1-(3-dimethylaminopropyl)-3-ethylcarbodiimide hydrochloride coupled with 1-hydroxybenzotriazole.

In the fourth step, deprotection of the imidazole nucleus of

Diagram 2

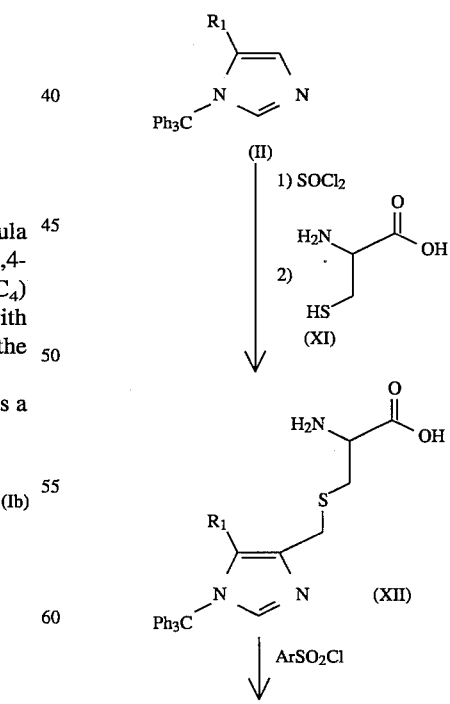

-continued
Diagram 2

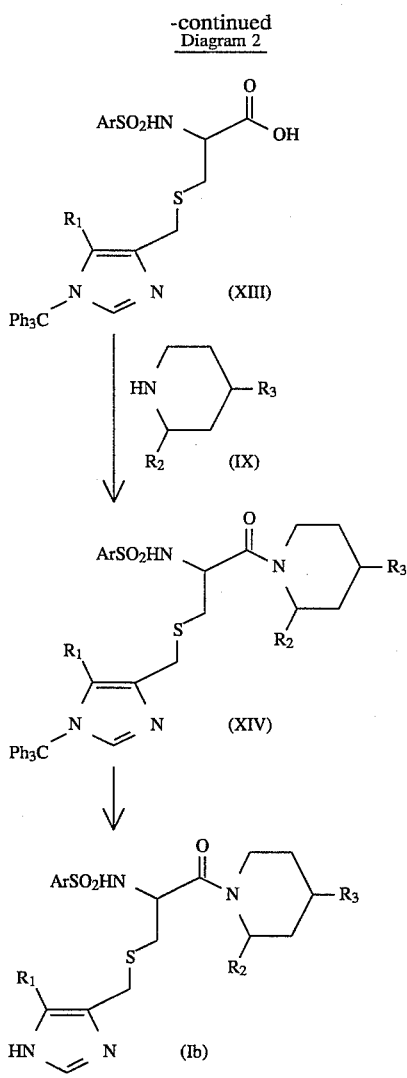

compound (XIV) is effected either by hydrogenation or by the action of acetic acid in a mixture of tetrahydrofuran and water. A compound of formula (Ib) is obtained. When a compound of formula (XIV) in which Ar represents the 3-methylquinolin-8-yl group is hydrogenated with heating, compounds of formula (Ib) are obtained, in which Ar is the 3-methyl-1,2,3,4-tetrahydroquinolin-8-yl group. When $R_2$ is a $(C_1-C_4)$alkoxycarbonyl group, compound (Ib) may be reacted with an aqueous solution of sodium hydroxide to obtain the sodium salt of the corresponding acid.

The compounds of formula (Ib) in which n=2 may be synthesised as shown in diagram 3 on the following page. In the first step, an alcohol of formula (II) is reacted with thionyl chloride in a mixture of dimethylformamide and dichloromethane, the compound thus obtained is then reacted with potassium thioacetate to provide a compound of formula (XV).

In the second step, compound (XV) is reacted with the tosylate of formula (XVI) to provide a compound of formula (XVII); the reaction is carried out in the presence of a base such as sodium methoxide. The tosylate of formula (XVI) is obtained by the action of paratoluenesulphonyl chloride, in the presence of a base, on the corresponding alcohol which itself is the precursor of the aldehyde of formula (IV), the synthesis of which is described by R. M. Valerio et al. in Synthesis, 1988, 786.

In the third step, the carboxylic moiety of the compound of formula (XVII) is deprotected using gaseous hydrogen chloride in benzene and a compound of formula (XVIII) is obtained. In the fourth step, compound of formula (XVIII) is condensed with a compound of formula (IX), to provide a compound of formula (XIX). The reaction is carried out in the presence of a base such as N-methylmorpholine or N,N-diisopropylethylamine ("Hünig's base") and a coupling agent such as (benzotriazol-1-yl)-oxy]tris(dimethylamino)phosphonium hexafluorophosphate, diphenylphosphorylazide or 1-(3-dimethylaminopropyl)-3-ethylcarbodiimide hydrochloride coupled with 1-hydroxybenzotriazole.

In the fifth step, the amino function of compound (XIX) is deprotected, either by the action of an acid or by hydrogenation, to provide a compound of formula (XX).

In the sixth step, a compound of formula (XX) is reacted with an arylsulphonyl chloride of the formula $ArSO_2Cl$ in which Ar is as defined above, to provide a compound of formula (XXI), this reaction being carried out in a solvent such as chloroform in the presence of base such as triethylamine. In the seventh step, deprotection of the imidazole nucleus of compound (XXI) is effected either by hydrogenation or by the action of acetic acid in a mixture of tetrahydrofuran and Diagram 3

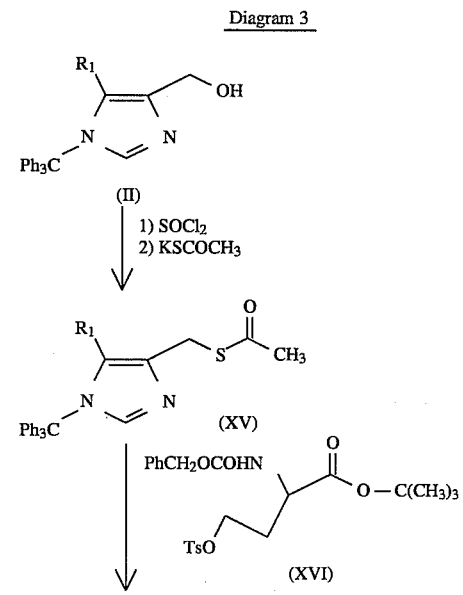

-continued
Diagram 3

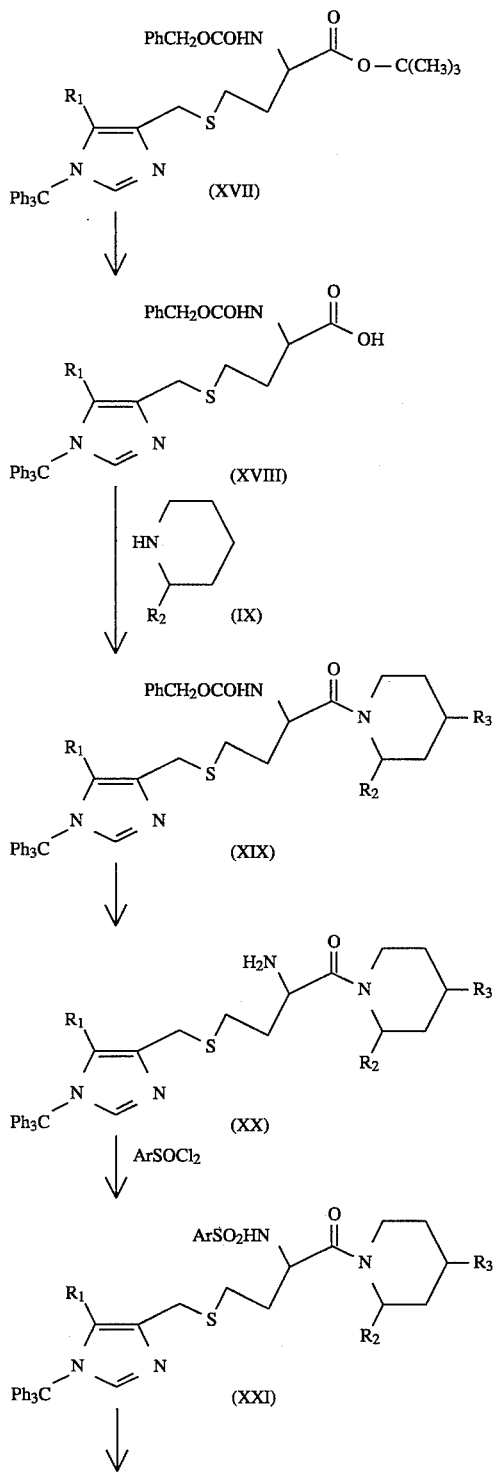

-continued
Diagram 3

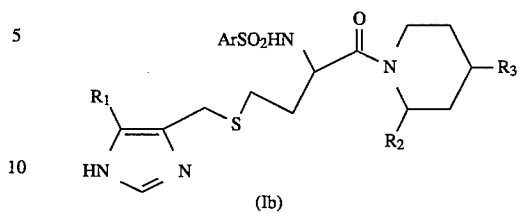

water. A compound of formula (Ib) is obtained.

When a compound of formula (XXI), in which Ar represents the 3-methylquinolin-8-yl group, is hydrogenated with heating, compounds of formula (Ib) are obtained, in which Ar is the 3-methyl-1,2,3,4-tetrahydroquinolin-8-yl group.

When $R_2$ is a $(C_1-C_4)$alkoxycarbonyl group, compound (Ib) may be reacted with a solution of sodium hydroxide to provide the sodium salt of the corresponding acid.

The compounds of the invention in which X represents an oxygen atom are of formula (Ic)

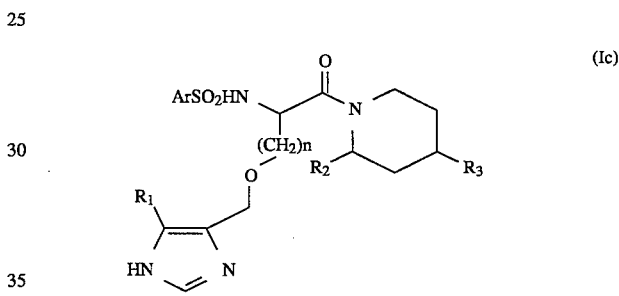

in which n=1 or 2 and $R_1$, $R_2$, $R_3$ and Ar are as defined above; they may be as synthesised as shown in diagram 4 on the following page.

In the first step, an alcohol of formula (II) is reacted with thionyl chloride in a mixture of dimethylformamide and dichloromethane; the compound obtained is then reacted with the sodium salt of a compound of formula (XXII), formed by the treatment of a compound of formula (XXII) with an excess of sodium hydride in tetrahydrofuran; in this way a compound of formula (XXIII) is obtained.

In the second step, a compound of formula (XXIII) is condensed with a compound of formula (IX), to provide a compound of formula (XXIV); the reaction is carried out in the presence of a base such as N-methylmorpholine or N,N-diisopropylethylamine ("Hünig's base") and a coupling agent such as [(benzotriazol-1-yl)-oxy]tris(dimethylamino)phosphonium hexafluorophosphate, diphenylphosphorylazide or 1-(3-dimethylaminopropyl)-3-ethylcarbodiimide hydrochloride coupled with 1-hydroxybenzotriazole.

In the third step, the primary amino function of compound of

Diagram 4

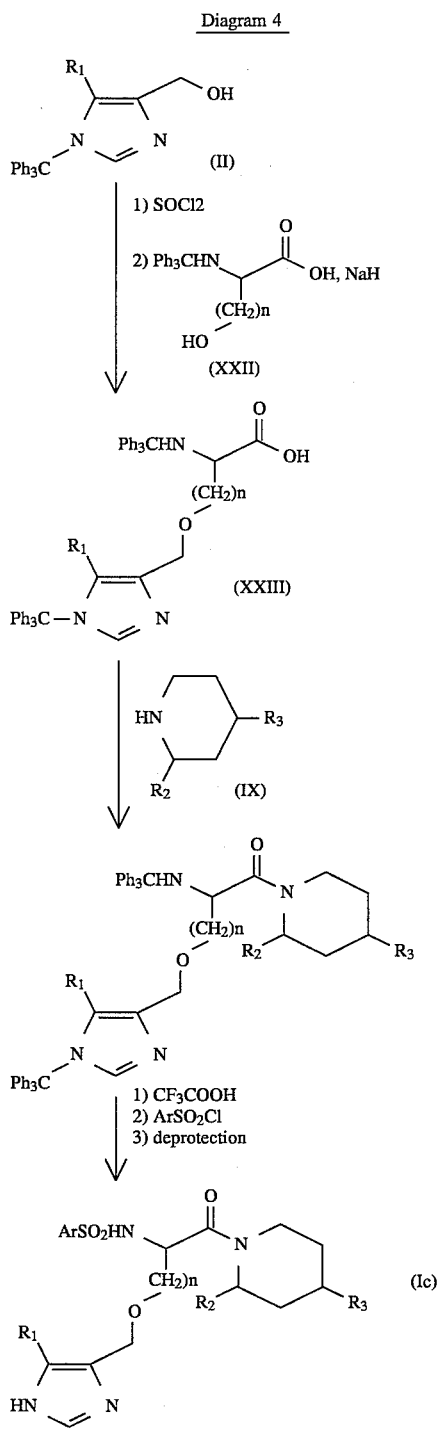

formula (XXIV) is firstly deprotected by the action of trifluoroacetic acid in a mixture of dichloroethane and methanol; an arylsulphonyl chloride of the formula ArSO$_2$Cl, in which Ar is as defined above, is then allowed to react in a solvent such as chloroform or dichloromethane in the presence of a base such as triethylamine. Finally, the imidazole nucleus of the compound of formula (XXIV) is deprotected by the action of acetic acid in a mixture of tetrahydrofuran and water to provide a compound of formula (Ic).

$N^2$-arylsulphonyl-L-argininamide derivatives, analogous compounds to those of the present invention, are described in European patent 0008746.

Starting materials used in the synthesis of compounds described herein are available commercially, or are described in the literature. They may be prepared by methods described therein or by methods known to persons skilled in the art.

The compounds of formula (II) are prepared by methods similar to those described in European patent 0242973 and those described by R. K. Griffith et al., Synthesis, 1983, 576. Some compounds of formula (IV) are described by R. M. Valerio et al., *Synthesis*, 1988, 786.

The preparation of 8-(chlorosulphonyl)-3-methylquinoline is described in Japanese patent application 59184161. 8-(Chlorosulphonyl)-3-methyl-1,2,3,4-tetrahydroquinoline may be prepared from 8-(chlorosulphonyl)-3-methylquinoline as follows: the 8-(chlorosulphonyl)-3-methylquinoline is first hydrolysed with an aqueous solution of sodium hydroxide, then, after acidification of the sodium sulphonate thus obtained, catalytic hydrogenation is carried out in the presence of a rhodium catalyst. The compound thus obtained, in the form of a triethylammonium salt, is then treated with the triphenylphosphine-sulphuryl chloride complex in a solvent such as dichloromethane.

The preparation of compounds of formula (IX), in which $R_2$ is a carboxylic or ethoxycarbonyl group and $R_3$ a methyl or ethyl group, is described in European patent 0008746. After chemical resolution with tartaric acid these compounds are obtained in the [2R,4R]form and are used in this form to prepare the other compounds of formula (IX).

Thus compounds of formula (IX), in which $R_2$ represents a —$CH_2OR_4$ group where $R_4$ is a hydrogen atom, may be synthesised as follows: a compound of formula (IX), in which $R_2$ is an ethoxycarbonyl group, is treated with bis(1,1-dimethylethyl) dicarbonate in a solvent such as dichloromethane under conventional conditions. The carboxyl function of the compound thus obtained is reduced, either by the mixed anhydride method described by R. M. Valerio et al., Synthesis, 1988, 786, or by the action of borane-dimethylsulphide complex in a solvent such as tetrahydrofuran. The amine functionality of the resulting compound is then deprotected directly by the action of trifluoroacetic acid, and a compound of formula (IX) is obtained in the form of a salt in which $R_2$ represents a —$CH_2OR_4$ group where $R_4$ is a hydrogen atom, and can be used as such in the next step.

Compounds of formula (IX) in which $R_2$ represents a —$CH_2OR_4$ group where $R_4$ is a ($C_1$-$C_4$)alkyl group may be synthesised as follows: a compound of formula (IX), in which $R_2$ represents a —$CH_2OR_4$ group where $R_4$ is a hydrogen atom, is reacted, in the presence of a base such as sodium hydride, with an alkyl halide of the formula $R_4$—X, in which $R_4$ is a ($C_1$-$C_4$)alkyl group and X is a halogen atom, preferably iodine. Deprotection of the amine function is carried out by the action of trifluoroacetic acid in dichloromethane, thus providing a compound of formula (IX) in which $R_2$ represents a —$CH_2OR_4$ group where $R_4$ is a ($C_1$-$C_4$)alkyl group in the form of a salt.

Thus compounds of formula (IX) in which $R_2$ represents a —$CH_2OR_4$ group, where $R_4$ is a ($C_1$-$C_4$)acyl group, may be prepared directly from compounds of formula (IX) in which $R_2$ represents a —$CH_2OR_4$ group where $R_4$ is a hydrogen atom by reaction with a ($C_1$-$C_4$)acyl chloride in the presence of a base such as triethylamine; deprotection of the amine functionality of the said compounds is effected by the action of trifluoroacetic acid to obtain a compound of formula (IX) in which $R_4$ is a $(C_1-C_4)$acyl group in the form of a salt which can be used directly.

Thus the compounds of formula (IX) in which $R_2$ represents a —$CONR_5R_6$ group, where $R_5$ is a hydrogen atom or a $(C_1-C_4)$alkyl group and $R_6$ is a hydrogen atom, a $(C_1-C_4)$alkyl group, a hydroxy group or a $(C_1-C_4)$alkoxy group, may be prepared as follows: a compound of formula (IX) in which $R_2$ is an ethoxycarbonyl group is treated with bis(1,1-dimethylethyl)dicarbonate, in a solvent such as dichloromethane, under conventional conditions. The compound thus obtained is saponified with an aqueous solution of sodium hydroxide, before being allowed to react with an amine of the formula $HNR_5R_6$, in which $R_5$ and $R_6$ are as defined above, thus providing an amide; the reaction is carried out in the presence of a base such as N-methylmorpholine or N,N-diisopropylethylamine ("Hünig's base") and a coupling agent such as [(benzotriazol-1-yl)oxy]tris(dimethylamino)phosphonium hexafluorophosphate or isobutylchloroformate. The amino group is deprotected by the action of trifluoroacetic acid in dichloromethane, possibly in the presence of anisole; the compounds thus obtained are in the form of a trifluoroacetate salt and are used as such in the next step.

Thus compounds of formula (IX), in which $R_2$ represents a —$CN_4R_5$ group where $R_5$ is a hydrogen atom, may be synthesised as follows: a compound of formula (IX), in which $R_2$ is a ethoxycarbonyl group, is treated with bis(1,1-dimethylethyl) dicarbonate in a solvent such as dichloromethane under conventional conditions. The compound thus obtained is condensed with ammonia, in the presence of a base such as N-methylmorpholine and a coupling agent such as isobutylchloroformate, in a solvent such as tetrahydrofuran. The carboxamide thus obtained is then dehydrated using phosphorus oxychloride to provide the corresponding nitrile which is then heated in the presence of sodium azide and ammonium chloride in a solvent such as dimethylformamide to provide the corresponding tetrazolyl derivative. The tetrazolyl derivative thus obtained is then treated with trifluoroacetic acid to provide a compound of formula (IX), in which $R_2$ represents a —$CN_4R_5$ group where $R_5$ is a hydrogen atom. Compounds of formula (IX), in which $R_2$ represents a —$CN_4R_5$ group where $R_5$ is a $(C_1-C_4)$alkyl group, may be synthesised as follows: a compound of formula (IX), in which $R_2$ represents a —$CN_4R_5$ group where $R_5$—X, is a hydrogen atom, is condensed with an alkyl halide of the formula $R_5$—X, in which $R_5$ is a $(C_1-C_4)$alkyl group and X is a halogen atom, preferably iodine; deprotection of the amine functionality is then accomplished by the action of trifluoroacetic acid in dichloromethane.

The compounds of formula (XXII) are described by Barlos et al., *J. Org. Chem.*, 1982, 47, 1324, and are treated as described by Barlos at al., *Tetrahedron*, 1983, 39, 475.

The following examples illustrate the preparation of some compounds according to the invention.

The structure of the compounds obtained were confirmed by $^1$H NMR spectroscopy and elemental analysis.

EXAMPLE 1

Ethyl [2R-[1(S),2α, 4β]]-4-methyl-1[2-[[3-methyl-1,2,3,4-tetrahydroquinolin-8-yl)sulphonyl]amino]-1-oxo-5-(1H-imidazol-4-yl)pentyl]piperidine-2-carboxylate 1.1. triphenyl[[(1-triphenylmethyl)-1H-imidazol-4yl]-methyl]phosphonium chloride 77.7 g (296 mmoles) of triphenylphosphine is added to solution of 105.5 g (294 mmoles) of 4-(chloromethyl)-1-(triphenylmethyl)-1H-imidazole in 670 ml of dimethylformamide.

The resulting mixture is heated at 80° C. for three hours. The solvent then is evaporated and the crude residue dissolved in ether and triturated. The precipitate is filtered and dried under vacuum over phosphorus pentoxide. 162 g of product is obtained in the form of yellowish crystals.

Melting point=210° C. Yield=89%

1.2. 1,1-dimethylethyl (S,E)-2[[(phenylmethoxy)carbonyl]amino]-5-[1-(triphenylmethyl)-1H-imidazol-4-yl]pent-4-enoate 50.93 g (820 mmoles) of triphenyl [[(1-triphenylmethyl)-1H-imidazol-4-yl]methyl]phosphonium chloride dissolved in 333 ml of tetrahydrofuran is placed in a three-necked flask under argon at −70° C.; 51.2 ml of a 1.6M solution of n-butyllithium in hexane (820 mmoles) is added in a dropwise fashion. After 30 minutes agitation at −70° C. the reaction medium is transferred rapidly into 270 ml of a 0.253M solution of 1,1-dimethylethyl (S)-4-oxo-2-[[(phenylmethoxy)-carbonyl]amino]butanoate in tetrahydrofuran (683 mmoles), at −70° C. The mixture is allowed to attain room temperature overnight. 280 ml of a saturated aqueous solution of sodium chloride is then added and the aqueous phase extracted twice with 140 ml of ethyl acetate. The combined organic phases are then dried over magnesium sulphate and evaporated to dryness. Purification by column chromatography using a hexane/ethyl acetate gradient provided the title compound 1.2 as a mixture of cis and trans olefins For the cis form: melting point=66° C. $R_f$=0.30 [hexane: ethyl acetate; 60:40]

For the trans form: $R_f$=0.15 [hexane: ethyl acetate; 60:40] Yield=40%

1.3. 1,1-dimethylethyl (S)-2-amino-5-[1-(triphenylmethyl)-1H-imidazol-4-yl]pentanoate hydrochloride 5.83 g (9.50 mmoles) of the cis compound obtained in paragraph 1.2 is dissolved in 120 ml of ethanol. Catalytic hydrogenation is carried out for five hours at 50 psi in the presence of palladium on charcoal as catalyst. The catalyst is filtered through a mixture of celite and silica and the solvent is evaporated. 4.32 g of product is collected and dissolved with heating in 90 ml of a 0.1 molar solution of HCl in isopropanol. The solvent is evaporated and the product precipitated with ether and dried under vacuum. 3.62 g of product is obtained.

Melting point=73° C. Yield=73%

1.4. 1,1-dimethylethyl (S)-2[[(3-methylquinolin-8-yl)sulphonyl]amino]-5-[1-(triphenylmethyl)-1H-imidazol-4-yl]pentanoate A solution of 1.76 g (7.28 mmoles) of 8-(chlorosulphonyl)- 3-methylquinoline in 50 ml of chloroform is added to 3.8 g (7.26 mmoles) of the compound obtained in paragraph 1.3 in the presence of 2.1 ml (14.5 mmoles) of triethylamine at 5° C. After stirring for three hours, the organic phase is separated, washed with a 0.1M solution of hydrochloric acid before being evaporated to dryness. The crude residue is purified by silica gel column chromatography using a mixture of ethanol and dichloromethane (5:95) as eluent to provide 3.6 g of product.

Melting point=56° C. Yield=72%

1.5. (S)-2[[(3-methylquinolin-8-yl)sulphonyl]amino]-5-[1-(triphenylmethyl)-1H-imidazol-4-yl]pentanoic acid Gaseous hydrogen chloride is bubbled for 15 minutes into a solution of 2.33 g (3.39 moles) of the compound obtained in paragraph 1.4 in 34 ml of benzene at 0° C., under nitrogen. The reaction medium is allowed to attain room temperature and is stirred for a further two hours. The solvent is evaporated under vacuum and the residue purified by silica gel column chomatography using a mixture of ethanol and dichloromethane (20:80) as eluent to provide 1.42 g of product in the form of a whitish powder.

Melting point=170° C. Yield=66%

1.6. Ethyl [2R-[1(S),2α, 4β]]-4-methyl-1-[2-[3-methylquinolin-8-yl)suphonyl]amino]-1-oxo-5-[1-(triphenylmethyl)-1H-imidazol-4-yl]pentyl]piperidin-2-carboxylate 1.56 g (3.53 mmoles) of [(benzotriazol-1-yl)oxy]tris(dimethylamino) phosphonium hexafluorophosphate, 0.78 ml (7.06 mmoles) of N-methylmorpholine, 0,61 g (3.57 mmoles) of ethyl (2R-trans)-4-methylpiperidine-2-carboxylate in 30 ml of dichloromethane are successively added to a suspension of 2.23 g (3.53 mmoles) of the compound obtained in paragraph 1.5 in 50 ml of acetonitrile, at 0° C. under nitrogen. The reaction is allowed to attain room temperature before being stirred for 5 hours. The reaction medium is hydrolysed with a saturated solution of sodium chloride and extracted with chloroform. The organic extracts are then washed successively with a 0.1N solution of hydrochloric acid, a saturated solution of sodium hydrogen carbonate, water and finally with a saturated solution of sodium chloride before being dried over magnesium sulphate and evaporated. The crude residue obtained is purified by silica gel column chromatography using a mixture of ethanol and dichloromethane (5:95) as eluent, to provide 1.94 g of product.

$R_f$=0.68 (dichloromethane: ethanol; 95:5)
Yield=70%

1.7. Ethyl [2R-[1(S),2α, 4β]]-4-methyl-1-[2-[3-methyl-1,2,3,4-tetrahydroquinolin-8-yl) sulphonyl]amino]-1-oxo-5-(1H-imidazol-4-yl)pentyl]-piperidine-2-carboxylate 17 ml of acetic acid is added to a solution of 1.94 g (2.47 mmoles) of the ester obtained in paragraph 1.6 in 70 ml of ethanol. Catalytic hydrogenation is then carried out in the presence of palladium on charcoal, at 80° C. for 6 hours. The mixture is filtered and the solvent evaporated. The residue obtained is dissolved in 1N hydrochloric acid, washed with ether and extracted with ethyl acetate. Evaporation of the solvent provided 1.05 g of product.

Melting point=104° C. (hydrochloride)
Yield=78%
$[\alpha]_D^{20}$=+101 (c=0.2; methanol)

EXAMPLE 2

Sodium salt of [2R-[1(S), 2α, 4β]]-4-methyl-1-[2-[[(3-methyl-1,2,3,4-tetrahydroquinolin-8-yl)sulphonyl]-amino]-1-oxo-5-(1H-imidazol-4-yl)pentyl]piperidine-2-carboxylate 0.4 ml of a standard 1N sodium hydroxide solution is added to a stirred solution of 0.201 g (0.360 mmole) of ester obtained in example 1 at room temperature under argon. Stirring is continued for 36 hours, the reaction being followed by thin layer chromatography. When the reaction is complete the reaction mixture is heated at 55° C. for seven hours, before being left to cool. Trituration using 1 ml of ethanol and 50 ml of ether provided a whitish precipitate which is filtered and dried.

170 mg of product is obtained in the form of a white powder.

Melting point=215° C. Yield=86% $[\alpha]_D$=+67.2 (C=0.1; methanol)

EXAMPLE 3

(R)-1-[2[[[5-(dimethylamino)naphthalen-1-yl]-sulphonyl]amino]-1-oxo-3-[[[(1H-imidazol-4-yl) methyl]thio]propyl]-4-ethylpiperidine hydrochloride

3.1. 2-amino-3-[[[1-(triphenylmethyl)-1H-imidazol-4-yl]methyl]thio]propanoic acid 2.66 g (22 Moles) of L-cysteine is added to 40 ml of a stirred 1N aqueous solution of sodium hydroxide (40 mmoles).

A solution of 7.2 g of 4-(chloromethyl)-1-(triphenylmethyl)- 1H-imidazole (20 mmoles) in 50 ml of ethanol and 20 ml of tetrahydrofuran is then added at 0° C. The temperature is allowed to rise to room temperature and the mixture stirred for 1 hour. The solvent is evaporated under reduced pressure and the residue dissolved in 100 ml of water and 20 ml of 1N hydrochloric acid. The precipitate obtained is filtered, washed with water, filtered and dried. 8 g of product is obtained.

Melting point=162°–164° C. (decomposition).
Yield=90%

3.2. (R)-2-[[[5-(dimethylamino)naphthalen-1-yl]-sulphonyl]-amino]-3-[[[1-triphenylmethyl)-1H-imidazol-4-yl]-methyl]thio]propanoic acid To a rapidly stirred solution of 1.77 g (4 mmoles) of the compound obtained in paragraph 3.1, in 20 ml of 0.2N sodium hydroxide, cooled in an ice bath, is added all at once, 1.08 g (4 mmoles) of 5-(dimethylamino)naphthalen-1-sulphonyl chloride. Stirring is continued for 30 minutes before 100 ml of water is added and the pH adjusted to 2.5 with a 1N solution of hydrochloric acid. The viscous precipitate obtained is drained and redissolved in dichloromethane before being dried over magnesium sulphate. After filtration and evaporation, the product is purified by silica gel column chromatography using a mixture of dichloromethane and methanol (95:5) as eluent.

1.2 g of product is obtained.

Melting point=128°–130° C. Yield=50%

3.3. (R)-1-[2-[[[5-(dimethylamino)naphthalen-1-yl]-sulphonyl]-amino]-1-oxo-3-[[[1-(triphenylmethyl)-1H-imidazol-4-yl]methyl]thio]propyl]-4-ethylpiperidine Protected from humidity and at 0° C., 1 g (1.5 mmoles) of the compound obtained in paragraph 3.2, 0.22 g (1.5 mmoles) of 4-ethylpiperidine hydrochloride and 0,663 g (1.5 mmoles) of [(benzotriazol-1-yl)oxy]tris(dimethylamino)phosphonium hexafluorophosphate are successively added to 15 ml of stirred acetonitrile. Stirring is continued and 0.34 ml (3.1 moles) of N-methylmorpholine is added. Stirring is continued overnight, before a saturated solution of sodium chloride is added. Extraction is carried out twice with ethyl acetate. The organic phase is washed successively with a 1N hydrochloric acid solution, water, a saturated solution of sodium bicarbonate and finally saturated sodium chloride solution before being dried over magnesium sulphate and evaporated under reduced pressure.

1 g of product is obtained and is used as such in the following step.

Melting point=99°–100° C. Yield=87%

3.4. (R)-1-[2[[[5-(dimethylamino)naphthalen-1-yl]-sulphonyl]amino]-1-oxo-3-[[[1-1H-imidazol-4-yl]methyl]-thio]propyl- 4-ethyl-piperidine hydrochloride A solution of 0.9 g (1.21 mmoles) of the compound obtained in paragraph 3.3, in 20 ml of 80% acetic acid, under nitrogen, is heated at reflux temperature for 20 minutes before being evaporated under reduced pressure.

The residue is purified by silica gel column chromatography using a mixture of dichloromethane and methanol (9:1) as eluent. 0.4 g of base is obtained.

A solution of HCl in isopropanol is then added to the residue and the hydrochloride salt obtained by crystallisation with diethylether.

0.15 g of product is obtained.

Melting point=105° C. (decomposition)
Yield=25%

$[\alpha]_D^{20}$=+99 (C=0.1; methanol)

EXAMPLE 4

(S)-4-ethyl-1-[4-[[(1H-imidazol-4-yl)methyl]-thio]-2-[[(3-methylquinolin-8-yl)sulphonyl]amino]-1-oxo-butyl]- piperidine hydrochloride

4.1. 1,1-dimethylethyl (S)-2-[[(phenylmethoxy)carbonyl]amino]-4-[[[1-(triphenylmethyl)-1H-imidazol-4-yl]methyl]-thio]butanoate 6 g of potassium thioacetate is added to a solution of 3.58 g (10 mmoles) of 4-(chloromethyl)-1-(triphenylmethyl)-1H-imidazole in 40 ml of ethanol under nitrogen. The reaction mixture is agitated by sonification for 15 minutes before being poured onto ether. The organic phase is washed successively with water, a saturated solution of sodium hydrogen carbonate, a saturated solution of sodium chloride, before being dried over magnesium sulphate and evaporated under reduced pressure. The residue is dissolved in 100 ml of methanol degassed with nitrogen and containing 1.9 ml (10 mmoles) of a 5.3N solution of sodium methoxide. After stirring for 15 minutes, a solution of 4.63 g (10 mmoles) of 1,1-dimethylethyl (S)-4[[4-methylphenyl)sulphonyl]-2[[(phenylmethoxy)carbonyl]amino]butanecarboxylate in 40 ml of degassed methanol is added. The reaction mixture is stirred for 24 hours at room temperature and the precipitate obtained is drained and washed with methanol and then with water. 3 g of product is obtained after drying.

Melting point=183-185° C. Yield=50%

4.2. (S)-2-[[phenylmethoxy)carbonyl]amino]-4-[[[1-(triphenylmethyl)-1H-imidazol-4-yl]methyl]thio]-butanoic acid hydrochloride 2.5 g (3.86 moles) of the compound obtained in paragraph 4.1 is placed in 50 ml of benzene. The solution protected from humidity is saturated with gaseous hydrogen chloride at 0° C. for 10 minutes. The reaction mixture is stirred for 2 hours at 0° C., before evaporation under reduced pressure.

2.2 g of product is obtained, and is used as such in the next step.

Melting point=78°–82° C. Yield=91%

4.3. (S)-4-ethyl-1-[1-oxo-2-[[(phenylmethoxy)carbonyl]-amino]-4-[[[1-(triphenylmethyl)-1H-imidazol-4-yl]methyl]thio]-butyl]piperidine 0.627 g (1 mmole) of the compound obtained in paragraph 4.2, 0.149 g (1 mole) of 4-ethylpiperidine hydrochloride and 0.442 g (1 mole) of [(benzotriazol-1-yl)oxy]tris(dimethylamino)phosphonium hexafluorophosphate in 15 ml of acetonitrile, protected from humidity, is added to 0.33 ml (3 mmoles) of N-methylmorpholine. Stirring is continued for 5 hours at room temperature before a saturated solution of sodium chloride is added and extraction carried out twice with ethyl acetate. The organic phases are combined, washed successively with water, a saturated solution of sodium bicarbonate and a saturated solution of sodium chloride before being dried over magnesium sulphate and evaporated under reduced pressure.

0.7 g of product is obtained in the form of an oil which crystallises with time.

Melting point=80°–82° C. Yield=100%

4.4. (S)-1-[2-amino-1-oxo-4-[[[1-(triphenylmethyl)-1H-imidazol-4-yl-]methyl]thio]butyl]-4-ethylpiperidine 0.7 g (1 mmole) of the compound obtained in paragraph 4.3 is placed in 1.2 ml of glacial acetic acid, under nitrogen at 10° C. 3 ml of a 4N solution of hydrobromic acid in acetic acid is added, protected from humidity. The reaction mixture is allowed to attain room temperature for 1 hour, protected from humidity, before being poured onto ether. The solid obtained is decanted off, washed with ether several times and dissolved in 5 ml of a mixture of dichloromethane and methanol. The mixture is brought to a basic pH with a few drops of concentrated aqueous ammonia. It is purified by silica gel column chromatography using a mixture of dichloromethane and ethanol (90:10) as eluent to provide 240 mg of product Melting point=115°–120° C. Yield=44%

4.5. (S)-4-ethyl-1-[2-[[(3-methylquinolin-8-yl)sulphonyl]-amino]-1-oxo-4-[[[1-(triphenylmethyl)-1H-imidazol-4-yl]-methyl]- thio]butyl]piperidine To a stirred solution of 0.23 g (0.418 mmole) of the compound obtained in paragraph 4.4 in 6 ml of dichloromethane protected from humidity is added 70 microliters (0.5 mmole) of triethylamine followed by 110 mg (0.6 mmole) of 8-(chloro-sulphonyl)-3-methyl-quinoline. The reaction mixture is stirred for 30 minutes at room temperature before being diluted with ethyl acetate. The reaction mixture is washed successively with a 1N solution of hydrochloric acid, water, a saturated solution of sodium bicarbonate, water and a saturated solution of sodium chloride before being dried over magnesium sulphate and evaporated under reduced pressure.

0.29 g of product is obtained and is used as such in the following step.

Melting point=84°–86° C. Yield=92%

4.6. (S)-4-ethyl-1-[4-[[1-H-imidazol-4-yl)methyl]thio]-2-[[(3-methylquinolin-8-yl)sulphonyl]amino]-1-oxobutyl]-piperidine hydrochloride 0.28 g (0.37 mmole) of the compound obtained in paragraph 4.5 is placed in 10 ml of an 80% aqueous solution of acetic acid, and 5 ml of tetrahydrofuran. The reaction mixture is heated under reflux for 15 minutes under nitrogen. The mixture is then evaporated under reduced pressure and the residue is purified by silica gel column chromatography using a mixture of dichloromethane and methanol as eluent. 0.16 g of product is obtained in the form of a base.

The hydrochloride is formed by the addition of a solution of HCl in isopropanol and is crystallised by the addition of diethylether.

0.14 g of product is obtained as crystals.

Melting point=70°–80° C. (decomposition)
Yield=66%
$[\alpha]_D^{20}$=+127° (C=+0.1; methanol)

EXAMPLE 5

Ethyl [2R-[1(S), 2α, 4β]]-1-[3-[1H-imidazol-4-yl)methoxy]-2[[(3-methyl-1,2,3,4-tetrahydroquinolin-8-yl)sulphonyl]amino]- 1-oxopropyl]-4-methyl piperidine-2-carboxylate

5.1. (N)-(triphenylmethyl)-(O)-[[1-(triphenylmethyl)-1H-imidazol- 4-yl]methyl]-(L)-serine acid 0.39 g (5.7 mmoles) of 4-(chloromethyl)-1-(triphenylmethyl)- 1H-imidazole followed by 10.01 g (28.83 mmoles) of (N)-(tri-phenylmethyl)-(L)-serine. To a stirred suspension of 5.8 g (144.2 mmoles) of sodium hydride (60%) in 112 ml of tetrahydrofuran, at −15° C. is added. Stirring is continued at −15° C. for 45 minutes before a further 12 g (34.6 mmoles) of 4-(chloromethyl)-1-(triphenylmethyl)-1H-imidazole is added. The reaction mixture is stirred for 2 hours at 0° C., followed by 5 hours at room temperature before being cooled to 0° C. when it was diluted with 200 ml of water and neutralised by adding 6.59 ml (115 mmoles) of acetic acid. It is decanted, and the aqueous phase is collected and extracted twice with 200 ml of ethyl acetate. The organic extracts are combined, washed with approximately 300 ml of water and dried over magnesium sulphate. The solvents are evaporated and the residue purified by silica gel column chromatography using an ethanol:dichloromethane gradient (2:98–4:96) as eluent.

Melting point=104°–106° C. Yield=68%

5.2. 2-[[(3-methyl-1,2,3,4-tetrahydroquinolin-8-yl)sulphonyl]amino]-(O)-[[1-(triphenylmethyl)-1H-imidazol- 4-yl]methyl]-(L)-serine acid 1.34 g (2 mmoles) of the compound obtained in paragraph 5.1. is placed in 26 ml of a mixture containing 95.5 % of 1,2-dichloroethane, 3% of methanol and 1.5% of trifluoroacetic acid at room temperature under nitrogen. The mixture is left to stand for a few minutes before 0.84 ml (6 mmoles) of triethylamine and a solution of 739 mg (3 mmoles) of 3-methyl-1,2,3,4-tetrahydroquinolin-8-sulphonyl chloride in 10 ml of chloroform are added at 0° C. Stirring is continued for one hour before the pH is adjusted to 3 with trifluoroacetic acid. The reaction mixture is purified by silica gel column chromatography using a mixture of chloroform and methanol (95:5) as eluent.

1.14 g of product is obtained.

Melting point=145°–150° C. Yield=91%

5.3. Ethyl[2R-[1(S),2α,4β]]-4-methyl-1-[2-[[(3-methyl-1,2,3,4-tetrahydroquinolin-8-yl)sulphonyl]amino]-1-oxo-3-[[1-(triphenylmethyl)-1H-imidazol-4-yl]methoxy]-propyl]- piperidine- 2-carboxylate To a solution of 1.2 g (1.94 mmoles) of the compound obtained in paragraph 5.2, 0,365 g (2.13 mmoles) of ethyl (2R-trans)-4-methylpiperidine-2-carboxylate and 0.950 g (2.15 mmoles) of ([benzotriazol-1-yl)oxy]tris(dimethylamino) phosphonium hexafluorophosphate in 15 ml of dichloromethane under nitrogen; at 0° C. is added 0.5 ml (2.87 mmoles) of N,N-diisopropylethylamine and stirring is continued overnight at room temperature. The reaction mixture is then diluted with 100 ml of ethyl acetate and is washed successively with 1M hydrochloric acid, water, a saturated solution of sodium bicarbonate and finally a saturated solution of sodium chloride, before being dried over magnesium sulphate. Evaporation of the solvents provides 1.2 g of product which is used as such in the following step.

Yield=80%

5.4. Ethyl [2R-[1(S), 2α, 4β]]-1-[3-[1H-imidazol-4-yl)methoxy]-2-[[(3-methyl-1,2,3,4-tetrahydroquinolin-8-yl)sulphonyl]amino]-1-oxopropyl]-4-methylpiperidine-2-carboxylate hydrochloride 1.2 g (1.55 mmoles) of the compound obtained in paragraph 5.3, in 20 ml of a (50/10/40) mixture of acetic acid, water and tetrahydrofuran are heated under gentle reflux for 45 minutes. After evaporation, the mixture is purified by silica gel column chromatography using a mixture of methanol and dichloromethane (5:95–10:90) as eluent which provides 0.6 g of product in the form of a base.

The hydrochloride is prepared by adding 300 mg of base to 6 ml of a 0.1N solution of hydrogen chloride in isopropanol and is crystallised using diethyl ether. The residue is drained and decanted to provide 180 mg of hydrochloride salt.

Melting point=62°–64° C. Yield=56%

EXAMPLE 6

(2R-trans)-N-ethyl-1-[5-(1H-imidazol-4-yl)-2[[(3-methyl-1,2,3,4-tetrahydroquinolin-8-yl)sulphonyl]amino]-1-oxopentyl]-4-methylpiperidine-2-carboxamide hydrochloride

6.1. (2R-trans)-N-ethyl-4-methylpiperidine-2-carboxamide trifluorocetate

6.1.1. 1,1-dimethylethyl (2R-trans)-2-(ethylamino)carbonyl]-4-methylpiperidine-1-carboxylate To a solution of 1 g (4.11 mmoles) of 1-(1.1-dimethylethyl) (2R-trans)-4-methylpiperidine-1,2 dicarboxylate in 15 ml of tetrahydrofuran at room temperature under argon is added 0.45 ml (4 mmoles) of N-methylmorpholine. The reaction mixture is then cooled to –10° C. –15° C. and 0.53 ml (4 mmoles) of 2-methylpropyl chloroformate is added, followed by 0.278 g (6 mmoles) of ethylamine dissolved in 3 ml of tetrahydrofuran. The temperature of the reaction mixture is allowed to rise to room temperature, before the tetrahydrofuran is evaporated. The residue is dissolved in 100 ml of ether and washed successively with 50 ml of 1N hydrochloric acid, 50 ml of water and finally with 50 ml of a solution saturated with sodium bicarbonate before being dried over magnesium sulphate and evaporated under reduced pressure to provide 1.06 g of product.

Yield=95%

6.1.2. (2R-trans)-N-ethyl-4-methylpiperidine-2-carboxamide trifluorocetate

To a solution of 0.352 g (1.3 mmoles) of the compound obtained in paragraph 6.1 in 5.4 ml of dichloromethane at 0° C. under argon, is added 5.4 ml of trifluoroacetic acid. The reaction mixture is allowed to rise to room temperature before evaporation. The residue is dissolved in 50 ml of dichloromethane and before being evaporated again to provide 0.686 g of crude product.

6.2. (S)-α-[[(3-methyl-1,2,3,4-tetrahydroquinolin-8-yl)sulphonyl]amino]-1-(triphenylmethyl)-1H-imidazole- 4-pentanoic acid

6.2.1. 3-methyl-1,2,3,4-tetrahydroquinolin-8-sulphonic acid 20 g (90 mmoles) of 3-methylquinoline-8-sulphonic acid is placed in a mixture of 200 ml of water and 25 ml of 12N hydrochloric acid. 6 g of 5% rhodium on charcoal catalyst is added and the reaction mixture is heated at 70° C. for 16 hours. The catalyst is filtered and washed with hot water and the filtrate is evaporated to provide a residue which is dissolved in 50 ml of ethanol. After evaporation of ethanol the residue is dried over phosphorus pentoxide at 50° C. 14 g of product is obtained.

Melting point=255° C. (decomposition)

6.2.2. ethyl (S)-α-[[(3-methyl-1,2,3,4-tetrahydroquinolin-8-yl)sulphonyl]amino]-1-(triphenylmethyl)-1H-imidazole- 4-pentanoate To a solution of 10.46 g (40 mmoles) of triphenylphosphine in 60 ml of dichloromethane at 0° C. under nitrogen, is added 3.56 ml (44 mmoles) of sulphuryl chloride in a dropwise fashion. The temperature is then allowed to rise to room temperature before a solution of 4.56 g (20 mmoles) of the compound obtained in paragraph 6.2.1, 100 ml of dichloromethane and 2.78 ml of triethylamine, is added over 10 minutes. The reaction mixture is stirred for a further hour at room temperature before being poured into 500 ml of pentane. The mixture is filtered and the filtrate is evaporated. The residue is dissolved in approximately 500 ml of pentane which is evaporated once more to provide 5 g of product in the form of an oil which is dissolved in 50 ml of dichloromethane. 35 ml of this solution is added to a solution of 4 g (7.72 mmoles) of ethyl (S)-α-amino-1-(triphenylmethyl)- 1H-imidazole-4-pentanoate hydrochloride in 50 ml of dichloromethane, under nitrogen at 0° C. The reaction mixture is allowed to stir for one hour before being washed successively with 50 ml of 1 N hydrochloric acid, 50 ml of water, 50 ml of a solution saturated with sodium bicarbonate, 50 ml of water and finally 50 ml of a saturated solution of sodium chloride. The solution is dried over magnesium sulphate before being evaporated under reduced pressure.

The residue is purified by silica gel column chromatography using dichloromethane: methanol (97:3) as eluent to provide 4.7 g of product.

Melting point: 70°–80° C. Yield=88% relative to the amine)

6.2.3. (S)-α-[[(3-methyl-1,2,3,4-tetrahydroquinolin-8-yl)sulphonyl]amino]-1-(triphenylmethyl)-1H-imidazole- 4-pentanoic acid A solution of 4.5 g (6.5 mmoles) of the compound obtained in paragraph 6 2 2 in 80 ml of benzene at 0° C. is bubbled with gaseous hydrogen chloride for one hour. Stirring is continued for a further 30 minutes at 0° C. before evaporation. The residue is dissolved in 10 ml of chloroform and the pH is adjusted to 8–9 with a solution of ammonia in dichloromethane. After evaporation, the residue is purified by silica gel column chromatography using a mixture of dichloromethane: methanol (95:5–90:10) as eluent to pro-

6.3. (2R-trans)-N-ethyl-4-methyl-1-[2-[[(3-methyl-1,2,3,4-tetrahydroquinolin-8-yl)sulphonyl]amino]-1-oxo-5-[1-triphenylmethyl)-1H-imidazol-4-yl]pentylpiperidine-2-carboxamide To a solution of 0,221 g (1.3 mmoles) of the compound obtained in paragraph 6.1 in 10 ml of dichloromethane at 0° C. under argon, is added successively 0.635 g (1 mmole) of the compound obtained in paragraph 6.2, 0,486 g (1.10 mmoles) of [(benzotriazol-1-yl)oxy]tris(dimethylamino)phosphonium hexafluorophosphate and 1.04 ml (6 mmoles) of N,N-diisopropylethylamine. The mixture is allowed to attain room temperature overnight before being washed successively with 10 ml of 1N hydrochloric acid and 10 ml of a solution saturated with sodium bicarbonate, dried over magnesium sulphate and evaporated to provide 0.337 g of product.

Melting point=30°–40° C. Yield=43%

6.4. (2R-trans)-N-ethyl-1-[5-(1H-imidazol-4-yl)-2-[[3-methyl-1,2,3,4-tetrahydroquinolin-8-yl)sulphonyl]amino]-1-oxopentyl]-4-methylpiperidine-2-carboxamide hydrochloride 0.332 g (0.422 mmole) of the compound obtained in paragraph 6.3. is dissolved in 3.7 ml of acetic acid; 0.7 ml of water and 3 ml of tetrahydrofuran are then added. The mixture is heated under reflux for one hour before being evaporated to dryness. Purification by silica gel column chromatography using dichloromethane:methanol gradient (90:10-85:15) as eluent provided 0.225 g of product in the form of a base. The hydrochloride is prepared by dissolving 0.225 g of base in 4.1 ml of 0.1M solution of hydrogen chloride in isopropanol. Evaporation is carried out and the residue is dissolved in ether. The material is filtered and dried. 0.200 g of of hydrochloride is obtained.

Melting point=105°–110° C. (decomposition)
$[\alpha]_D^{20}=+33.2$ (c=0.2; methanol)

EXAMPLE 7

2R-[1(H), 2α, 4β]]-N-hydroxy-1-[5-(1S-imidazol-4-yl)-2-[[(3-methyl-1,2,3,4-tetrahydroquinolin-8-yl)sulphonyl]amino]-1-oxopentyl]-4-methylpiperidine-2-carboxamide hydrochloride

7.1. (2R-trans)-4-methyl-N-(phenylmethoxy)piperidine-2-carboxamide trifluoroacetate

7.1.1. (2R-trans)-1-(2,2-dimethyl-1-oxopropyl)-4-methylpiperidine-2-carboxylic acid To a solution of 0.51 g (3 mmoles) of ethyl (2R-trans)-4-methylpiperidine-2-carboxylate in 10 ml of dichloromethane at 0° C. under nitrogen is added 654 mg (3 mmoles) bis(1,1-dimethylethyl) dicarbonate. The temperature is allowed to rise to room temperature overnight. After evaporation, the residue is dissolved in 4 ml of ethanol and 3 ml of a 1M solution of sodium hydroxide. It is left overnight at room temperature and a further 3 ml of a 1N solution of sodium hydroxide is added. Evaporation is carried out and the residue dissolved in water and washed with ether. The aqueous phase is acidified with 1M hydrochloric acid and extraction is carried out twice with ether. The organic phase is then rinsed with 10 ml of a solution saturated with sodium chloride before being dried over magnesium sulphate and evaporated. 0.68 g of product is obtained.

Melting point=87°–90° C. Yield=97%

7.1.2. (2R-trans)-1-(2,2-dimethyl-1-oxopropyl)-4-methyl-N-(phenylmethoxy)piperidine-2-carboxamide To a stirred solution of 1 g (4.03 mmoles) of the compound obtained in paragraph 7.1.1. in 15 ml of tetrahydrofuran at −15° C. under nitrogen is added 0.47 ml (4 mmoles) of N-methylmorpholine and 0.56 ml (4 mmoles) of 2-methylpropyl chloroformate. Stirring is continued for 5 minutes before a solution of 0,755 g (4.7 mmoles) of O-(phenylmethyl)hydroxylamine hydrochloride in a mixture of 5 ml of tetrahydrofuran and 0.52 ml of N-methylmorpholine, is added. Stirring is continued at room temperature overnight before being poured onto 3 volumes of ethyl acetate. The organic phase is washed successively with 50 ml of 0.1N hydrochloric acid, 50 ml of water, 50 ml of sodium hydrogen carbonate, 50 ml of water and finally with 50 ml of a saturated solution of sodium chloride before being dried over magnesium sulphate, evaporated and crystallised by trituration in ether. 0.95 g of product is obtained.

Melting point=107°–108° C.

7.1.3. (2R-trans)-4-methyl-N-(phenylmethoxy)piperidine-2-carboxamide trifluoroacetate A solution of 450 mg (1.4 mmoles) of the compound obtained in paragraph 7.1.2. in a mixture of 5 ml of trifluoroacetic acid and 5 ml of dichloromethane is stirred for 15 minutes at 0° C. After evaporation, the residue is dissolved in 10 ml of benzene and evaporation is carried out once again. 700 mg of product is obtained, in the form of an oil which is used as such in the next step.

7.2. [2R-[1(S), 2α, 4β]]-N-hydroxy-1-[5-(1H-imidazol-4-yl)-2[[(3-methyl-1,2,3,4-tetrahydroquinolin-8-yl)sulphonyl]amino]-1-oxopentyl]-4-methylpiperidine-2-carboxamide hydrochloride

7.2.1. [2R-[1(S), 2α, 4β]]-4-methyl-1-[2-[[(3-methyl-1,2,3,4-tetrahydroquinolin-8-yl)sulphonyl]amino]-1-oxo-5-[1-(triphenylmethyl)-1H-imidazol-4-yl]pentyl]-N-(phenylmethoxy)-piperidine-2-carboxamide To a stirred solution of 700 mg (1.4 mmoles) of the compound obtained in paragraph 7.1 in 10 ml of dichloromethane at 0° C. under nitrogen was added successively, 630 mg (1 mmole) of the compound obtained in paragraph 6.2, 500 mg (1.13 mmoles) of [(benzotriazol-1-yl)oxy]tris(dimethylamino)phosphonium hexafluorophosphate and 0.875 (5 mmoles) of N,N-diisopropylethylamine. The mixture was stirred at room temperature overnight, before being poured onto 80 ml of ethyl acetate. The organic phase is washed successively with 80 ml of 0.1M hydrochloric acid, 80 ml of water, 80 ml of a solution of sodium bicarbonate and finally with 80 ml of a saturated solution of sodium chloride, before being dried over magnesium sulphate and evaporated. The residue is purified by silica gel column chromatography using a mixture of dichloromethane and methanol (97:3) as eluent to provide 0.8 g of product.

Melting point=90°–100° C. Yield=93%

7.2.2. [2R-[(S), 2α, 4β]]-1-[5-(1H-imidazol-4-yl)-2-[[(3-methyl-1,2,3,4-tetrahydroquinolin-8-yl)sulphonyl]amino]-1-oxopentyl]-4-methyl-N-phenylmethoxy)piperidine-2-carboxamide A solution of 0.8 g (0.93 mmole) of the compound obtained in paragraph 7.2.1 in 10 ml of tetrahydrofuran and 10 ml of 80% acetic acid is heated under reflux under nitrogen. After evaporation the residue is dissolved in 10 ml of dichloromethane and purified by silica gel column chromatography using mixture of dichloromethane and methanol (9:1) as eluent to provide 0.5 g of product.

Melting point=75°–95° C. Yield=88%

7.2.3. [2R-[1(S), 2α, 4β]]-N-hydroxy-1-[5-(1H-imidazol-4-yl)-2-[[(3-methyl-1,2,3,4-tetrahydroquinolin-8-yl)sulfonyl]-amino]-1-oxopentyl]-4-methyl piperidin-2-carboxamide hydrochloride 0.45 g (0.73 mmole) of the compound obtained in paragraph 7.2.2. is placed in 30 ml of methanol, 0.1 g of 10 % palladium catalyst is added and hydrogenation is carried out for 10 hours at 40 psi. The catalyst is drained, evaporation is carried out and the residue purified by silica gel column chromatography using mixture of dichloromethane and methanol (9:1) as eluent.

0.2 g of product is obtained, in the form of a base. The hydrochloride is prepared by the addition of a solution of hydrogen chloride in isopropanol. It is crystallised using ethanol to provide 0,15 g of hydrochloride.

$[\alpha]_D^{20}$=+85 (c=0.1; methanol).

EXAMPLE 8

[2R-[1(S), 2α, 4β]]-1-[5-(1H-imidazol-4-yl)-2-[[(3-methyl-1,2,3,4-tetrahydroquinolin-8-yl)-sulphonyl]amino]-1-oxopentyl]-4-methyl-2-(1H-tetrazol-4-yl)piperidine hydrochloride

8.1. (2R-trans)-4-methyl-2-(1H-tetrazol-4-yl)piperidine trifluoroacetate

8.1.1. (2R-trans)-1-(2,2-dimethyl-1-oxopropyl)-4-methylpiperidine-2-carboxamide To a solution of 1 g (4.03 mmoles) of the compound obtained in paragraph 7.1.1. in 15 ml of tetrahydrofuran at −15° C. under nitrogen, is added 0.47 ml (4 mmoles) of 4-methylmorpholine followed by 0.56 ml (4 mmoles) of 2-methylpropyl chloroformate. The mixture is stirred for 5 minutes before an excess of ammonia is bubbled in. The reaction mixture is allowed to rise to room temperature and stirring is continued for one hour. It is poured into 3 volumes of ethyl acetate and washed successively with 50 ml of 0.1M hydrochloric acid, 50 ml of water, 50 ml of a solution of sodium bicarbonate, 50 ml of water and finally with 50 ml of a saturated solution of sodium chloride before being dried over magnesium sulphate and evaporated.

1 g of product is obtained, in the form of an opaque oil which is used as such in the next step.

8.1.2. (2R-trans)-1-(2,2-dimethyl-1-oxopropyl)-4-methylpiperidine-2-carbonitrile To a solution of 1 g (4 mmoles) of the compound obtained in paragraph 8.1.1 in 5 ml of pyridine at −5° C. is added carefully 0.52 ml of phosphoryl chloride in 1 ml of dichloromethane. The reaction mixture is stirred for one hour before being poured onto ice. Extraction is effected by 100 ml of diethyl ether. After evaporation the residue is purified by silica gel column chromatography using dichloromethane as eluent. 0.7 g of product is obtained, in the form of an oil which is used as such in the next step.

8.1.3. (2R-trans)-4-methyl-2-(1-H-tetrazol-4-yl)piperidine

A mixture of 0.7 g (3.1 mmoles) of the compound obtained in paragraph 8.1.2, 212 mg (3 mmoles) of sodium azide and 180 mg (4 mmoles) of ammonium chloride in 1.5 ml of dimethylformamide is placed in a sealed tube. The mixture is heated at 100° C. for 24 hours before evaporation is carried out. The residue is dissolved in a mixture of sodium carbonate solution and diethyl ether, the organic phase is separated and the pH of the aqueous phase is adjusted to 2 with 1N hydrochloric acid. Extraction is carried out with diethyl ether and the organic phase dried over magnesium sulphate, and evaporated. 0.3 g of product is obtained, in the form of an oil which is used as such in the next step.

8.1.4. (2R-trans)-4-methyl-2-(1H-tetrazol-4-yl)piperidine trifluoroacetate

To a solution of 242 mg (0.9 mmole) of the compound obtained in paragraph 8.1.3. in 2 ml of dichloromethane, under nitrogen is added 2 ml of trifluoroacetic acid. The mixture is stirred for 1 hour at room temperature before being evaporated. The residue is dissolved in dichloromethane, evaporation is carried out once again to provide 355 mg of product obtained in the form of an oil which is used as such in the next step.

8.2.[2RR-[1(S),2α,4β]]-1-[5-(1H-imidazol-4-yl)-2-[[(3-methyl-1,2,3,4-tetrahydroquinolin-8-yl)-sulphonyl]-amino]-1-oxopentyl]-4-methyl-2-(1H-tetrazol-4-yl)-piperidine hydrochloride

8.2.1. [2R-[1(S), 2α, 4β]]-4-methyl-1-[2-[[(3-methyl-1,2,3,4-tetrahydroquinolin-8-yl)sulphonyl]amino]-1-oxo-5-[ 1-(triphenylmethyl)-1H-imidazol-4-yl]pentyl]-2-(1H-tetrazol-4-yl)piperidine To a stirred solution of 355 mg (0.9 mmole) of the compound obtained in paragraph 8.1 in 6 ml of dichloromethane, under nitrogen, is added successively 435 mg (0.98 mmole) of [(benzotriazol-1-yl)oxy]tris(dimethylamino)phosphonium hexafluorophosphate, 0.7 ml (5.64 mmoles) of N,N-diisopropylethylamine and 570 mg of the compound obtained in paragraph 6.2. The reaction mixture is allowed to stir at room temperature overnight before being poured onto 50 ml of ethyl acetate. The organic phase is washed successively with 50 ml of 0.1N hydrochloric acid, 50 ml of water and finally with 50 ml of a saturated solution of sodium chloride before being dried over magnesium sulphate and evaporated. The residue is then dissolved in 3 ml of dichloromethane, the pH of which has been adjusted to 5 with ammonia. After evaporation, the residue is purified by silica gel column chromatography using mixture of silica gel column dichloromethane and methanol (97:3) as eluent.

450 mg of product is obtained.

Melting point=120°–130° C. Yield=63%

8.2.2. [2R-[1(S), 2α, 4β]]-1-(5-(1H-imidazol-4-yl)-2-[[(3-methyl-1,2,3,4-tetrahydroquinolin-8-yl)sulphonyl]amino]-1-oxopentyl]-4-methyl-2-(1H-tetrazol-4-yl)piperidine hydrochloride A mixture of 450 mg (0.57 mmole) of the compound obtained in paragraph 8.2.1. in a mixture of 5 ml of acetic acid, 1 ml of water and 4 ml of tetrahydrofuran is heated under reflux for 45 minutes under nitrogen. Evaporation is carried out and the residue is purified by silica gel column chromatography using a mixture of dichloromethane and methanol (9:1-8:2) as eluent 200 mg of product in form of a base is obtained.

The hydrochloride is prepared from the base when it has been purified by silica gel column chromatography using a mixture of water/0.1% trifluoroacetic acid/acetonitrile (gradient of 95:5-5:95) as eluent. The required fractions are combined and evaporated. The residue is dissolved in a 0.1N solution of hydrogen chloride in isopropanol and evaporated again. The residue is dissolved in ether and triturated to provide 0.15 g of product as a hydrochloride salt.

Melting point=140°–150° C.

$[\alpha]_D^{20}$=+115 (c=0.2; methanol).

The following table illustrates the chemical structures and physical properties of some compounds according to the invention.

TABLE

| No | Ar | X | n | R₁ | R₂ | R₃ | Salt | $[\alpha]_D^{20}$ (c, methanol) | MPt (°C.) |
|---|---|---|---|---|---|---|---|---|---|
| 1 | 1-naphthyl-N(CH₃)₂ | —CH₂— | 1 | —H | —H | —CH₃ | Ox | +62,9 (0,14) | 103 |
| 2 | 1-naphthyl-N(CH₃)₂ | —CH₂— | 1 | —H | —H | —CH₂CH₃ | HCl | +49,6 (0,12) | 105–110 |
| 3 | 1-naphthyl-N(CH₃)₂ | —CH₂— | 1 | —CH₃ | —H | —CH₃ | HCl | +132,9 (0,15) | 74 |
| 4 | 1-naphthyl-N(CH₃)₂ | —S— | 1 | —H | —H | —CH₂CH₃ | HCl | +99,0 (0,1) | 105 (d) |

TABLE-continued

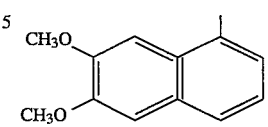

(I)

| No | Ar | X | n | R₁ | R₂ | R₃ | Salt | $[\alpha]_D^{20}$ (c, methanol) | MPt (°C.) |
|---|---|---|---|---|---|---|---|---|---|
| 5 | 6,7-dimethoxynaphthalen-1-yl (CH₃O, CH₃O on naphthalene) | —CH₂— | 1 | —H | —H | —CH₂CH₃ | HCl | +30,4 (0,25) | 55–60 |
| 6 | 3-methyl-1,2,3,4-tetrahydroquinolin-8-yl | —CH₂— | 1 | —H | —H | —CH₃ | Ox | +98 (0,2) | 108 |
| 7 | 3-methyl-1,2,3,4-tetrahydroquinolin-8-yl | —CH₂— | 2 | —H | —H | —CH₃ | Ox | +127,2 (0,12) | 94–95 |
| 8 | 3-methyl-1,2,3,4-tetrahydroquinolin-8-yl | —S— | 1 | —H | —H | —CH₂CH₃ | HCl | +149 (0,1) | 70–80 |
| 9 | 3-methyl-1,2,3,4-tetrahydroquinolin-8-yl | —S— | 2 | —H | —H | —CH₂CH₃ | HCl | +127 (1,0) | 70–80 |
| 10 | 3-methyl-1,2,3,4-tetrahydroquinolin-8-yl | —CH₂— | 1 | —H | —CO₂CH₂CH₃ | —CH₃ | HCl | +101 (0,2) | 104 |
| 11 | 3-methyl-1,2,3,4-tetrahydroquinolin-8-yl | —CH₂— | 1 | —H | —CO₂H | —CH₃ | Na | +67,2 (0,1) | 215 |
| 12 | 1H-indazol-7-yl | —CH₂— | 1 | —H | —H | —CH₂CH₃ | HCl | +52 (0,1) | 192–195 |

TABLE-continued (I)

$$ArSO_2HN-\underset{(CH_2)_n}{\underset{|}{CH}}-\underset{R_1}{\overset{O}{\overset{\|}{C}}}-R \quad R=-N\underset{R_2}{\overset{R_3}{\bigcirc}}$$

(with imidazole-CH$_2$-X- substituent)

| No | Ar | X | n | R$_1$ | R$_2$ | R$_3$ | Salt | [α]$_D^{20}$ (c, methanol) | MPt (°C.) |
|---|---|---|---|---|---|---|---|---|---|
| 13 | 3-methyl-1,2,3,4-tetrahydroquinolin-N-yl | —CH$_2$— | 1 | —CH$_3$ | —CO$_2$H | —CH$_3$ | Na | +36 (0,1) | 210 (d) |
| 14 | 3-methyl-1,2,3,4-tetrahydroquinolin-N-yl | —CH$_2$— | 1 | —CH$_3$ | —CO$_2$CH$_2$CH$_3$ | —CH$_3$ | HCl | +67,5 (0,2) | 80 |
| 15 | 3-methyl-1,2,3,4-tetrahydroquinolin-N-yl | —S— | 1 | —H | —CO$_2$CH$_2$CH$_3$ | —CH$_3$ | HCl | +126 (0,1) | 108 (d) |
| 16 | 3-methyl-1,2,3,4-tetrahydroquinolin-N-yl | —S— | 1 | —H | —CO$_2$H | —CH$_3$ | Na | +41,5 (0,2) | 190–195 (d) |
| 17 | 3-methyl-1,2,3,4-tetrahydroquinolin-N-yl | —S— | 1 | —H | —CO$_2$CH$_3$ | —CH$_3$ | HCl | +57,0 (0,1) | 100–105 |
| 18 | 3-methyl-1,2,3,4-tetrahydroquinolin-N-yl | —O— | 1 | —H | —CO$_2$H | —CH$_3$ | HCl | +78 (0,2) | 104–108 |
| 19 | 3-methyl-1,2,3,4-tetrahydroquinolin-N-yl | —O— | 1 | —H | —CO$_2$CH$_2$CH$_3$ | —CH$_3$ | HCl | +71,0 (0,1) | 62–64 |
| 20 | 3-methyl-1,2,3,4-tetrahydroquinolin-N-yl | —CH$_2$— | 1 | —H | —CONH$_2$ | —CH$_3$ | HCl | +77 (0,1) | 115 |

TABLE-continued (I)

$$ArSO_2NH-\underset{(CH_2)_n}{\underset{|}{CH}}-\underset{}{\overset{O}{\overset{\|}{C}}}-R \quad R = -N\underset{R_2}{\overset{}{\underset{}{\bigcirc}}}R_3$$

with imidazole (R₁) substituent

| No | Ar | X | n | R₁ | R₂ | R₃ | Salt | $[\alpha]_D^{20}$ (c, methanol) | MPt (°C.) |
|---|---|---|---|---|---|---|---|---|---|
| 21 | 3-methyl-1,2,3,4-tetrahydroquinolin-8-yl | —CH₂— | 1 | —H | —CO₂CH₃ | —CH₃ | HCl | +69,5 (0,2) | 120–125 (d) |
| 22 | 3-methyl-1,2,3,4-tetrahydroquinolin-8-yl | —CH₂— | 1 | —H | —CONHCH₂CH₃ | —CH₃ | HCl | +33,2 (0,2) | 105–110 (d) |
| 23 | 3-methyl-1,2,3,4-tetrahydroquinolin-8-yl | —CH₂— | 1 | —H | —CON(CH₃)₂ | —CH₃ | HCl | +67,0 (0,5) | 98 |
| 24 | 3-methyl-1,2,3,4-tetrahydroquinolin-8-yl | —CH₂— | 1 | —H | —CONHOH | —CH₃ | HCl | +121 (0,1) | 105 |
| 25 | 3-methyl-1,2,3,4-tetrahydroquinolin-8-yl | —CH₂— | 1 | —H | —CONHOH | —CH₃ | HCl | +85 (0,1) | 140 (d) |
| 26 | 3-methyl-1,2,3,4-tetrahydroquinolin-8-yl | —CH₂— | 1 | —H | —CON(CH₃)OH | —CH₃ | HCl | +73 (0,2) | 110–115 |
| 27 | 3-methyl-1,2,3,4-tetrahydroquinolin-8-yl | —CH₂— | 1 | —H | —CONHOCH₃ | —CH₃ | HCl | +91,0 (0,2) | 103 |
| 28 | 3-methyl-1,2,3,4-tetrahydroquinolin-8-yl | —CH₂— | 1 | —H | —CH₂OH | —CH₃ | HCl | +73,7 (0,1) | 92–94 |

TABLE-continued

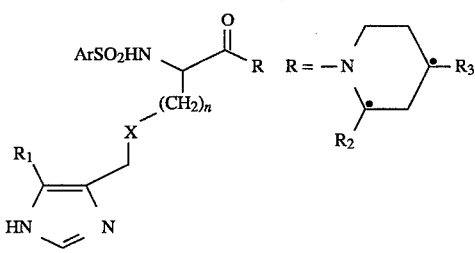
(I)

| No | Ar | X | n | R₁ | R₂ | R₃ | Salt | [α]$_D^{20}$ (c, methanol) | MPt (°C.) |
|---|---|---|---|---|---|---|---|---|---|
| 29 | (8-methyl-3-methyl-tetrahydroquinolinyl) | —CH₂— | 1 | —H | —CH₂OCH₃ | —CH₃ | HCl | +82,5 (0,2) | 105–107 |
| 30 | (8-methyl-3-methyl-tetrahydroquinolinyl) | —CH₂— | 1 | —H | —CN₄H | —CH₃ | HCl | +115 (0,2) | 140–150 |
| 31 | (8-methyl-3-methyl-tetrahydroquinolinyl) | —CH₂— | 1 | —CH₃ | —CO₂CH₂CH₃ | —CH₂CH₃ | HCl | +151 (0,2) | 97–103 |
| 32 | (8-methyl-3-methyl-tetrahydroquinolinyl) | —CH₂— | 1 | —CH₃ | —CH₂OCOCH₃ | —CH₃ | HCl | +125 (0,2) | 68–72 |
| 33 | (8-methyl-3-methyl-tetrahydroquinolinyl) | —CH₂— | 1 | —H | —CH₂OCOCH₃ | —CH₃ | HCl | +98 (0.2) | 64–65 |
| 34 | (8-methyl-3-methyl-tetrahydroquinolinyl) | —CH₂— | 1 | —CH₃ | —CH₂OH | —CH₃ | HCl | +109 (0.2) | 120–124 |
| 35 | (8-methyl-3-methyl-tetrahydroquinolinyl) | —CH₂— | 1 | —CH₃ | —CO₂H | —CH₂CH₃ | HCl | +95 (0.2) | 190–195 |

Note:
in column "R₂": —CN₄H represents a 1H-tetrazolyl group;
in column "Salt": "ox" signifies oxalate, "HCl" signifies hydrochloride and "Na" signifies sodium salt; +L6 in column "MPt (°C.)": (d) signifies decomposition.

The compounds of the invention have been tested with thrombin and trypsin in vitro in the following tests:
1. Precipitation of human fibrinogen by bovine thrombin
The compound to be tested or its vehicle (10 μl) is incubated for 2 minutes at 37° C., in a solution of human fibrinogen (200 μl, 2 mg per ml in physiological saline). 200 μl of bovine thrombin is 0.5 NIH units per ml. It is agitated and the time, in seconds, required for the formation of a visible fibrin network is noted. Inhibition of fibrin formation is quantified by calculating the concentration of compound which increases the precipitation time by 100% ($CA_{100}$). The results are expressed in $CA_{100}$, (mean ±s.e.m.) of at least three experiments.

2. Precipitation of human fibrinogen by human thrombin

The compound to be tested or its vehicle (10 μl) is incubated for 2 minutes at 37° C., in a solution of human fibrinogen (200 μl, 2 mg per ml in physiological saline). 200 μl of human thrombin dissolved in distilled water is then added. The final concentration of the thrombin is 2 NIH units per ml. It is agitated and the time, in seconds, required for the formation of a visible fibrin network is noted. Inhibition of fibrin formation is quantified by calculating the concentration of compound which increases the precipitation time by 100% ($CA_{100}$). The results are expressed in $CA_{100}$, (mean ±s.e.m.) of a least three experiments.

3. Coagulation of rat plasma by bovine thrombin

Male CD rats weighing 150 to 200 g are anaesthetized with nembutal (60 mg/kg, 0.1 ml/kg). Blood is taken in the presence of 3.8% trisodium citrate (1 vol per 9 volumes of blood) from the retro orbital sinus. The plasma is prepared by centrifugation at 3600 g for 15 minutes at room temperature. The compound to be tested or its vehicle (10 μl) is incubated with 200 μl of plasma at 37° C. for 2 minutes, before the addition of 200 μl of a solution of bovine thrombin. The final concentration of the thrombin is 0.75 NIH units per ml. The coagulation time expressed in seconds, is noted. Inhibition of thrombin is quantified by calculating the concentration which increases the coagulation time by 100% ($CA_{100}$).

4. Aggregation of rabbit platelets induced by human thrombin

Blood is taken by cardiac puncture in the presence of 3.8% trisodium citrate (1 volume per 9 volumes of blood). It is centrifuged at 250 g for 10 minutes. The plasma rich in platelets (PRP) thus obtained is retained, and the platelets are numbered.

Prostacyclin (2 ng per ml), dissolved in ice-cold tris buffer at pH 9.0, is added to the PRP, which is then centrifuged at 110 g for 10 minutes and the supernatant is decanted. The platelets are resuspended in tyrrode's solution containing prostacyclin, dissolved in 50 mM sodium hydroxide at pH 12, so as to have a final concentration of 200 ng per ml. The PRP is centrifuged again at 800 g for 10 minutes. The platelet poor plasma is removed, and the residue is suspended in a volume equal to the initial volume of PRP of tyrode's solution containing 200 ng/ml prostacyclin. The suspension is centrifuged at 800 g for 10 minutes. Resuspension of the platelet pellet and centrifugation are repeated a second time under the same conditions. The final residue is re-suspended in tyrode's solution without prostacyclin to be degraded. Aggregation of the platelets is induced with human thrombin at the final concentration of 0.3 NIH unit per ml. Variations in optical density are recorded by means of a 4-channel aggregometer. The compound to be tested or its vehicle is added to the platelet suspension (maximum volume added 3 μl), 2 minutes before the thrombin is added. The concentration which inhibits aggregation by 50% ($IC_{50}$) is determined. The results are expressed in $IC_{50}$, (mean ±s.e.m.) of at least 3 experiments.

5. Activity against bovine trypsin

The compound to be tested or its vehicle (50 μl) is incubated for 5 minutes at room temperature with 50 μl of bovine trypsin dissolved in tris HCl buffer at pH 8.0. The final concentration of trypsin is 229 units per ml. The reaction is initiated by adding substrate, Ne-benzoyl-L-arginine-4 nitroaniline (50 μl, final concentration 50 μM). Incubation is carried out for 20 minutes at room temperature, and the optical density of the 4-nitro-aniline liberated is measured at 405 nm. The concentration of 4-nitro-aniline is calculated from a calibration curve, after subtracting the optical density of the blanks (100 μl of buffer plus 50 μl of substrate). The concentration which inhibits enzyme activity by 50% is determined ($IC_{50}$). The results are expressed as $IC_{50}$ (mean ±s.e.m.).

The compounds of the invention have also been tested against rat plasma coagulation ex-vivo. The animals are treated with the compound to be tested or its medium, intravenously or orally, before the blood is taken. The thrombin time is measured as described in paragraphe 3.

The compounds of the invention are thrombin inhibitors with $CA_{100}$ and $IC_{50}$ levels from $10^{-9}$ to $10^{-6}$M. They have little or no inhibition activity against bovine trypsin, which demonstrates their specificity. They inhibit coagulation of rat plasma in doses below 1 mg per kg intravenously and are also active orally.

The compounds of the invention may be useful in any clinical indications connected with thrombosis or in cases where thrombotic complications may arise. For this purpose they may be provided in any form appropriate for oral, parenteral or intravenous administration, such as tablets, capsules, suspensions, drinkable or injectable solutions, etc., combined with appropriate excipients and dosed so as to allow for administration of 1 to 1000 mg per day per patient, in one or more doses.

We claim:

1. A compound of formula (I)

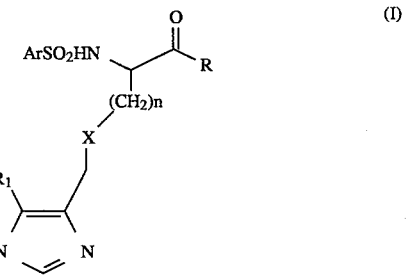

wherein R represents a

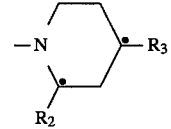

group in which $R_2$ is a hydrogen atom, a $(C_1-C_4)$alkoxycarbonyl group, a carboxylic group, a sodium carboxylate group, a —$CH_2OR_4$ group $R_4$ being a hydrogen atom or a $(C_1-C_4)$alkyl group or a $(C_1-C_4)$acyl group, an amide group of the formula —$CONR_5R_6$, or a —$CN_4R_5$ group, $R_5$ being a hydrogen atom or a $(C_1-C_4)$alkyl group and $R_6$ being a hydrogen atom, a $(C_1-C_4)$alkyl group, a hydroxy group or a $(C_1-C_4)$alkoxy group, and $R_3$ is a $(C_1-C_4)$alkyl group, $R_1$ represents either a hydrogen atom or a $(C_1-C_4)$alkyl group, X represents either a sulphur atom, an oxygen atom or a methylene group, n=1 or 2 and Ar represents either a quinolin-8-yl group substituted at 3 by a $(C_1-C_4)$alkyl group, or a 1,2,3,4-tetrahydroquinolin-8-yl group substituted at 3 by a (C₁–C₄)alkyl, group or a pharmaceutically acceptable organic or inorganic salt thereof.

2. A compound according to claim 1, wherein R represents a

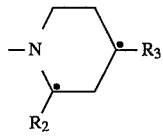

group in which $R_2$ is a hydrogen atom, a $(C_1-C_4)$alkoxycarbonyl group, a carboxylic group, a sodium carboxylate group, a —CH₂OR₄ group R₄ being a hydrogen atom or a $(C_1-C_4)$alkyl group or a $(C_1-C_4)$acyl group, an amide group of the formula —CONR₅R₆, or a —CN₄R₅ group, R₅ being a hydrogen atom or a $(C_1-C_4)$alkyl group and R₆ being a hydrogen atom, a $(C_1-C_4)$alkyl group, a hydroxy group or a $(C_1-C_4)$alkoxy group, and R₃ is a $(C_1-C_4)$alkyl group, $R_1$ represents either a hydrogen atom or a $(C_1-C_4)$alkyl group, X represents either a sulphur atom, an oxygen atom or a methylene group, n=1 or 2 and Ar represents either the 5-(dimethylamino)naphtalen-1-yl group, or the 6,7-dimethoxynaphthalen-1-yl group, or the 3-methylquinolin-8-yl group, or the 3-methyl-1,2,3,4-tetrahydroquinolin-8-yl group, the compounds possibly being in the form of diastereoisomers.

3. A compound according to claim 2, wherein R represents a

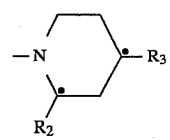

group in which R₂ is a carboxylic group, an ethoxycarbonyl group, a hydroxycarboxamide group, a hydroxymethyl group, or a 1H-tetrazolyl group, and R₃ is a methyl group or an ethyl group, R₁ is a hydrogen atom or a methyl group, X is a methylene group, n=1 and Ar is the 3-methyl-1,2,3,4-tetrahydroquinolin-8-yl radical.

4. A compound according to claim 1, wherein the configuration of the piperidinyl group is [2R, 4R] and the configuration of the asymmetric carbon in the central amino part

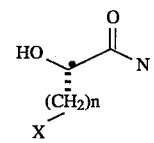

is [S].

5. A pharmaceutical composition, wherein it comprises an effective amount of a compound according to claim 1, in combination with any appropriate excipient.

* * * * *